(12) United States Patent
Kemme et al.

(10) Patent No.: US 8,238,026 B1
(45) Date of Patent: Aug. 7, 2012

(54) POLARIZATION-SENSITIVE INFRARED IMAGE SENSOR INCLUDING A PLURALITY OF OPTICAL FIBERS

(75) Inventors: Shanalyn A. Kemme, Albuquerque, NM (US); Alvaro A. Cruz-Cabrera, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 720 days.

(21) Appl. No.: 12/364,537

(22) Filed: Feb. 3, 2009

(51) Int. Cl.
*G02B 27/28* (2006.01)
(52) U.S. Cl. .............. 359/489.17; 359/489.07; 250/225; 250/341.3; 356/367
(58) Field of Classification Search .......................... None
See application file for complete search history.

(56) References Cited

U.S. PATENT DOCUMENTS

| | | | |
|---|---|---|---|
| 5,890,095 A | 3/1999 | Barbour et al. | |
| 6,410,917 B1* | 6/2002 | Choi .......................... | 250/338.4 |
| 6,563,582 B1 | 5/2003 | Chun | |
| 7,173,698 B2 | 2/2007 | Gerhart et al. | |
| 7,186,968 B2 | 3/2007 | Raynor | |
| 2003/0133113 A1* | 7/2003 | Hajduk et al. ................ | 356/367 |
| 2006/0223032 A1* | 10/2006 | Fried et al. ................... | 433/215 |
| 2007/0241267 A1 | 10/2007 | Gruev et al. | |

FOREIGN PATENT DOCUMENTS
JP   06180282 A  *  6/1994

OTHER PUBLICATIONS

Gregory P. Nordin et al, "Micropolarizer array for infrared imaging polarimetry", J. Opt. Soc. Am. A, 1999, vol. 16, pp. 1168-1174.
James A. Harrington, et al, "Infrared Fiber Optics", http://irfibers.rutgers.edu/pdf_files/ir_fiber_review.pdf, 2000.
Shanalyn A. Kemme, "Micropolarizing Device for Long Wavelength Infrared Polarization Imaging", SAND2006-6889, 2008.
Robert R. Boye et al, "Fabrication and measurement of wideband achromatic waveplates for the mid-infrared region using subwavelength features", J. Microlith., Microfab., Microsyst., vol. 5, No. 4, (Oct.-Dec. 2006).
R. R. Boye et al, "Pixilated Wideband Achromatic Waveplates Fabricated for the Mid IR Using Subwavelength Features", Proc. of SPIE, vol. 6127, (2006) pp. 612709-1 thru 612709-10.

(Continued)

*Primary Examiner* — Arnel C Lavarias
(74) *Attorney, Agent, or Firm* — Lowell Carson (57) ABSTRACT

A polarization-sensitive infrared image sensor (also termed a snapshot polarimeter) utilizing a 2-D array of polarizers to filter infrared light from a scene according to polarization, and a 2-D array of photodetectors (i.e. a focal plane array) to detect the filtered infrared light and generate polarization information which can be used to form a polarization-sensitive image of the scene. By forming each polarizer on an optical fiber in a fiber optic faceplate, the polarizers can be located facing a 2-D array of retarders to minimize diffraction effects of the infrared light. The optical fibers also guide the filtered infrared light to the photodetectors to reduce crosstalk in the polarization information. The polarizers can be formed as wire grid polarizers; and the retarders can be formed as subwavelength surface-relief gratings.

25 Claims, 5 Drawing Sheets

OTHER PUBLICATIONS

A. A. Cruz-Cabrera et al, "Polarimetric Imaging Cross Talk Effects from Glue Separation between FPA and Micropolarizer Arrays at the MWIR", Proc of SPIE vol. 6478, Feb. 9, 2007, pp. 647800-1 thru 647800-13.

S. A. Kemme et al, "Micropolarizer Arrays in the MWIR for Snapshot Polarimetric Imaging", International Semiconductor Conference, Lausanne, France, Oct. 15-17, 2007, Proc of SPIE vol. 6556, May 3, 2007, pp. 655604-1 thru 655604-11.

A. A. Cruz-Cabrera et al, "3-D Fiber faceplates to mitigate diffraction effects in an imaging snapshot polimeter", Proc of SPIE vol. 6972, Mar. 31, 2008, pp. 697204-1 thru 697204-7.

* cited by examiner

POLARIZATION-SENSITIVE INFRARED IMAGE SENSOR INCLUDING A PLURALITY OF OPTICAL FIBERS

GOVERNMENT RIGHTS

This invention was made with Government support under Contract No. DE-AC04-94AL85000 awarded by the U.S. Department of Energy. The Government has certain rights in the invention.

FIELD OF THE INVENTION

The present invention relates to imaging polarimeters, and in particular to snapshot polarimeters which simultaneously measure different polarization states of an image using infrared light.

BACKGROUND OF THE INVENTION

There is currently a significant level of interest in extending the capabilities of infrared imaging systems beyond conventional amplitude imaging to include polarimetry which provides additional information which can be used to highlight or suppress different materials in a scene, or objects at different orientations. Polarimetry can be useful, for example, to distinguish man-made objects in a scene from natural objects. The usual method for imaging polarimetry is to sequentially measure each polarization component of an image, and then to use these measurements to calculate the Stokes parameters in order to characterize the polarization state of each pixel in the image. However, this sequential method does not allow polarization-sensitive imaging of dynamically-changing scenes due to movement of the imaging system, or due to movement of objects within the scene, or both.

A number of different approaches have been developed for imaging polarimetry as detailed in U.S. Pat. Nos. 5,890,095; 7,173,698; 7,186,968; and in U.S. Pat. Appl. Pub. 2007/0241267. These approaches have met with limited success.

The present invention provides an advance in the art by providing a polarization-sensitive infrared imaging sensor which utilizes fiber optics to reduce the cross-talk between adjacent pixels of an infrared image in the sensor, and thereby improve an extinction ratio of the sensor. The sensor of the present invention utilizes a two-dimensional (2-D) array of polarizers which are fabricated directly on the end of a plurality of optical fibers. The optical fibers can be formed as a fiber optic faceplate. A 2-D array of infrared phase retarders can be formed on a substrate and attached directly to the fiber optic faceplate to minimize the distance between the retarders and the polarizers to minimize the distance therebetween and thereby minimize diffraction effects which could otherwise result in crosstalk between adjacent pixels of the infrared image in the sensor. The fiber optic faceplate can be attached directly onto a focal plane array to form a compact and rugged integrated unit, with the optical fibers guiding infrared light to photodetectors in the focal plane array while minimizing the cross-talk between adjacent pixels of the infrared image.

The polarization-sensitive infrared imaging sensor of the present invention allows polarization information to be extracted from the infrared image in real-time, and allows the polarization information to be presented in parallel with intensity information. This is useful to form a super pixel image of a scene in which all four of the Stokes parameters are simultaneously measured, thereby eliminating noise which could otherwise occur due to scene movement if sequential measurements of the Stokes parameters were to be made.

These and other advantages of the present invention will become evident to those skilled in the art.

SUMMARY OF THE INVENTION

The present invention relates to a polarization-sensitive infrared image sensor which comprises a 2-D array of polarizers to receive infrared light from a scene and to filter the infrared light according to polarization. A 2-D array of optical fibers is located proximate to the 2-D array of polarizers to receive the filtered infrared light from each polarizer at an entrance end of the 2-D array of optical fibers and to transmit the filtered infrared light to an exit end of the optical fibers. A 2-D array of infrared photodetectors (also referred to herein as a focal plane array) is located proximate to the exit end of the 2-D array of optical fibers, with each infrared photodetector detecting the filtered infrared light from one of the optical fibers to generate an electrical output signal containing polarization information for a pixel of the scene. The electrical output signals from a plurality of adjacent infrared photodetectors in the 2-D array of photodetectors can be input into a signal processor to form a super pixel of a polarization-sensitive image of the scene. A display can be connected to the signal processor to display the polarization-sensitive image of the scene. Infrared light from the scene can be imaged onto the sensor using imaging optics comprising one or more lenses or mirrors.

The polarization-sensitive infrared image sensor can further comprise a 2-D array of retarders (also referred to as retardation plates, wave plates or phase plates) which are located in front of the 2-D array of polarizers to provide an optical phase shift of the infrared light prior to filtering of the infrared light by the polarizers. Each retarder is generally a quarter-wave plate, and can be formed using a subwavelength surface-relief grating.

The 2-D array of optical fibers can be formed as a fiber optic faceplate. The fiber optic faceplate can include an infrared-absorbing material disposed between the optical fibers therein, and can further include an anti-reflection coating on an exit side of the fiber optic faceplate. Each polarizer generally comprises a wire grid polarizer, and can formed on the entrance end of one of the optical fibers (e.g. on each optical fiber in the fiber optic faceplate).

The present invention further relates to a polarization-sensitive infrared image sensor which comprises a 2-D array of wire grid polarizers to receive an infrared light image of a scene and to divide the infrared light image into a plurality of pixels with each pixel being filtered according to polarization by one of the wire grid polarizers. The sensor also includes an infrared fiber optic faceplate comprising a 2-D array of optical fibers which is located proximate to the 2-D array of wire grid polarizers and with each optical fiber receiving one of the pixels and directing that pixel to an exit end of that optical fiber where an infrared photodetector is located. The infrared photodetector senses the pixel and generates therefrom an electrical output signal containing polarization information for that pixel. A signal processor can be connected to the sensor to receive and combine the electrical output signals from a plurality of adjacent infrared photodetectors to form a super pixel of a polarization-sensitive image of the scene which can then be displayed with a display (e.g. a computer monitor).

The 2-D array of wire grid polarizers can be formed on an entrance side of the infrared fiber optic faceplate with each wire grid polarizer being centered about one of the optical fibers. The optical fibers in the infrared fiber optic faceplate can be separated by an infrared-absorbing material. A retarder can also be located proximate to at least one of the wire grid polarizers to provide an optical phase shift of the infrared light for the pixel being filtered by that wire grid polarizer. The retarder can comprise a subwavelength surface-relief grating.

The present invention also relates to a polarization-sensitive infrared image sensor which comprises a substrate having a plurality of retarders formed thereon, with the plurality of retarders being spaced apart, and with each retarder providing an optical phase shift for infrared light from a scene which is incident on that retarder. An infrared fiber optic faceplate can be located proximate to the plurality of retarders, with the infrared fiber optic faceplate having an entrance side and an exit side and comprising a plurality of optical fibers extending therebetween. A plurality of wire grid polarizers can be formed on the entrance side of the infrared fiber optic faceplate, with each wire grid polarizer being centered about one of the optical fibers to filter the infrared light according to polarization, with the polarization-filtered infrared light then being transmitted through that optical fiber to the exit side. A focal plane array detector, which comprises a 2-D array of infrared photodetectors, can be located proximate to the exit side of the infrared fiber optic faceplate, with each infrared photodetector being located proximate to one of the optical fibers to detect the polarization-filtered infrared light transmitted through that optical fiber to generate an electrical output signal therefrom. A signal processor can then be used to combine the electrical output signals from a plurality of the infrared photodetectors which are adjacent to each other to generate a polarization-sensitive image of the scene.

Infrared imaging optics comprising one or more lenses or mirrors can be used to image the infrared light from the scene onto the plurality of retarders. Each retarder can comprise a subwavelength surface-relief grating.

The infrared fiber optic faceplate can include an infrared-absorbing material disposed between the optical fibers therein, and can further include an anti-reflection coating on the exit side thereof. The focal plane array detector can be attached to the exit side of the infrared fiber optic faceplate; and the substrate containing the retarders can be attached to the entrance side of the infrared fiber optic faceplate.

Additional advantages and novel features of the invention will become apparent to those skilled in the art upon examination of the following detailed description thereof when considered in conjunction with the accompanying drawings. The advantages of the invention can be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several aspects of the present invention and, together with the description, serve to explain the principles of the invention. The drawings are only for the purpose of illustrating preferred embodiments of the invention and are not to be construed as limiting the invention. In the drawings.

DETAILED DESCRIPTION OF THE INVENTION

Figure 1:
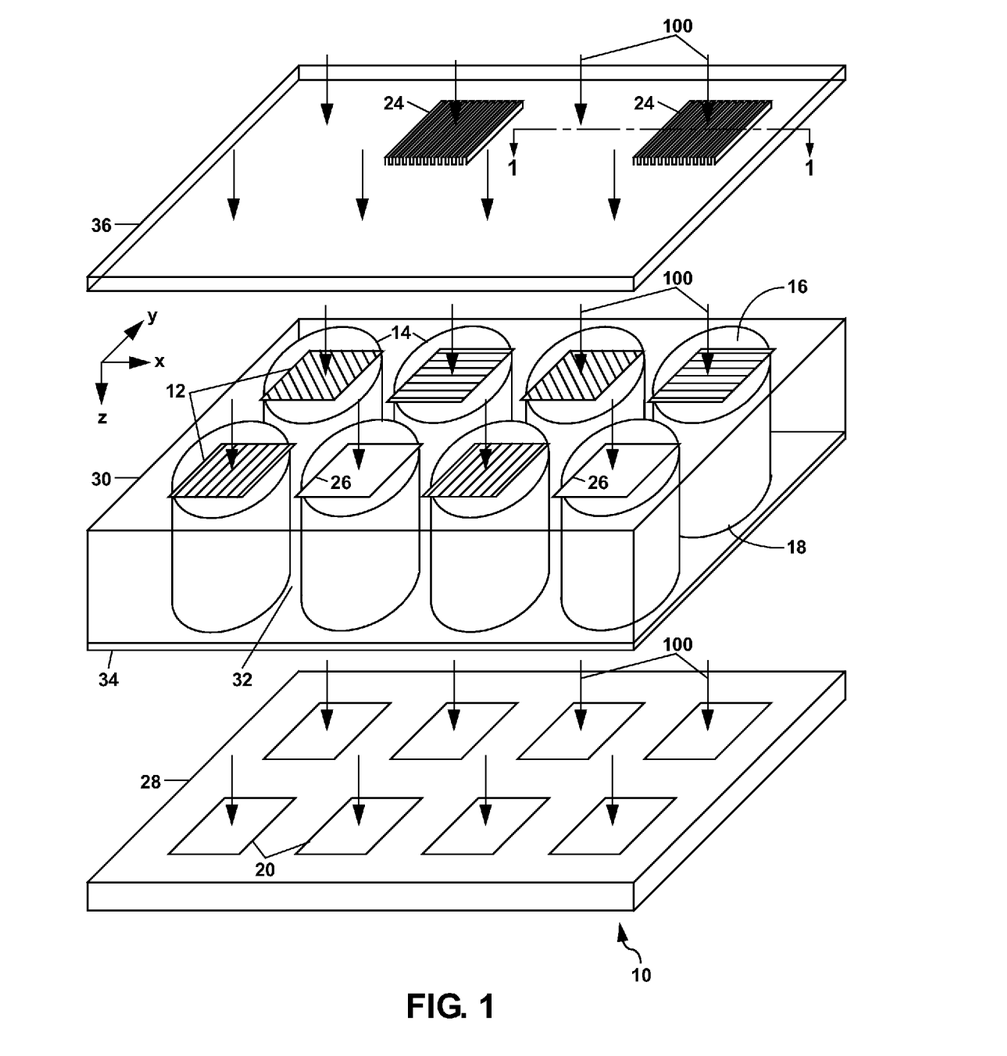
FIG. 1 shows an exploded perspective view of a first example of the polarization-sensitive infrared imaging sensor of the present invention.

Referring to FIG. 1, there is shown an exploded perspective view of a first example of the polarization-sensitive infrared imaging sensor 10 of the present invention. The sensor 10 comprises a plurality of polarizers 12 which can be arranged in a two-dimensional (2-D) array to filter infrared light 100 received from a scene 110 (see FIG. 3) and imaged onto the 2-D array of polarizers 12. Each polarizer 12 filters the infrared light 100 according to polarization for a pixel of the infrared image of the scene 110 which is incident on that polarizer 12.

In FIG. 1, a 2-D array of optical fibers 14 is located proximate to the polarizers 12 to receive the filtered infrared light 100 from each polarizer 12 at an entrance end 16 of the optical fibers 14, with the optical fibers 14 transmitting the filtered infrared light 100 to an exit end 18 of the fibers 14. The polarizers 12 can be formed directly on the entrance end 16 of the optical fibers 14 as shown in FIG. 1.

A 2-D array of infrared photodetectors 20 (i.e. an infrared focal plane array) is located proximate to the exit end 18 of the optical fibers 14 in FIG. 1, with each photodetector 20 detecting the filtered infrared light 100 from one of the optical fibers 14 to generate an electrical output signal 22 which contains polarization information for the infrared light 100 in that pixel of the image of the scene 110. The polarization information can then be used to generate a polarization-sensitive image of the scene 110.

The reflection of light from the surface of an object changes the polarization of the light in a way which depends upon the shape of the object, the type of material from which the object is made, and the orientation of the object relative to an observer. As a result, different objects in a scene 110 will have different polarization signatures which are useful, for example, to determine whether the object is a man-made object or a natural object. Thus, by measuring the polarization of light reflected from objects in the scene 110 together with the intensity of the light, the polarization-sensitive infrared image sensor 10 of the present invention can be used to distinguish man-made objects from natural objects. This can be used, for example, to distinguish buildings and vehicles in the scene 110 from trees and shrubs, even when the buildings and vehicles are partially obscured by the trees and shrubs. This is useful for surveillance, reconnaissance and target identification.

The polarization properties of light can be fully described by a set of parameters known as Stokes parameters. The polarization state of light can be described by the Stokes vector $\overline{S}$, which is a four element real vector comprising the Stokes parameters $S_0$, $S_1$, $S_2$ and $S_3$ which can be expressed as:

$$\bar{S} = \begin{matrix} S_0 \\ S_1 \\ S_2 \\ S_3 \end{matrix}$$

The first Stokes parameter $S_0$ represents the intensity of the light. The remaining Stokes parameters $S_1$, $S_2$ and $S_3$ describe the polarization state of the light and give the preference for horizontal versus vertical polarization, for linear polarization oriented along 45° and 135° measured with respect to the horizontal direction, and the preference for right-circular and left-circular polarization, respectively. The Stokes parameters can be determined by measuring the intensity of light which is transmitted through a plurality of linear polarizers which are oriented in different directions and through a retarder. When the Stokes parameters are normalized by dividing by $S_0$, each Stokes parameter has a value between −1 and +1.

The polarization-sensitive infrared imaging sensor 10 of the present invention is useful to collect infrared light 100 from a scene 110 and to process the infrared light 100 to separate out the various polarization components of the infrared light 100 which can then be used to determine the Stokes parameters to provide a full polarization characterization of the scene 110, or to separately display a particular Stokes parameter which provides sufficient contrast to distinguish between man-made and natural objects in the scene 110.

Those skilled in the art will understand that there are many different ways of representing the above Stokes parameters depending upon how the polarizers and one or more retarders are arranged for a set of pixels of an infrared image which are used to provide the polarization information needed to calculate the Stokes parameters. To obtain the full set of four Stokes parameters as listed above, the infrared image of the scene 110 can be divided into a plurality of sets of four pixels of the which are simultaneously filtered by three or four polarizers 12 having different orientations together with a retarder 24 which is located proximate to one of the polarizers 12 to distinguish between right-circular and left-circular polarization. In some embodiments of the present invention where it is not necessary to differentiate between right-circular and left-circular polarization, the retarders 24 can be omitted and only three Stokes parameters determined (i.e. $S_0$, $S_1$ and $S_2$).

FIG. 1 shows a first example of a polarization-sensitive infrared imaging sensor 10 of the present invention which utilizes three polarizers 12 having polarization axes which are oriented at 0°, 45° and 90° with respect to an x-axis (also referred to as a horizontal axis) of the sensor 10. Each polarizer 12 filters a particular polarization of the infrared light 100 from the scene 110 which is imaged thereon, with the amount of the light 100 being transmitted through each polarizer 12 depending upon the orientation of that polarizer 12 relative to a direction of oscillation of the electric field vector of the light 100, which forms a pixel of the infrared image, and further depending upon whether the light 100 is linearly polarized or circularly polarized. Thus, the polarizers 12 simply filter the infrared light 100 for each pixel of the infrared image of the scene 110 without altering the polarization of the light 100. This is in contrast to the retarders 24 which can alter the polarization of the infrared light 100.

In FIG. 1, a plurality of spaces 26 (also referred to as open cells) are provided where no polarizer 12 is present so that the photodetectors 20 below these open cells 26 can be used to detect the intensity $I_T$ of the infrared light 100 independent of polarization to determine $S_0$. In the example of FIG. 1, a plurality of retarders 24 are also shown located above the polarizers 12 which are oriented at 0° (also termed horizontal polarizers).

In the example of FIG. 1, only a small number of elements 12, 14, 20, 24 and 26 are shown to allow these elements to be enlarged for clarity. In the actual sensor 10, there can be up to tens of thousands or more individual elements 12, 14, 20, 24 and 26 depending upon a predetermined number of pixels in the infrared image of the scene 110 (e.g. from 256×256 to 1024×1024 or more pixels).

With the orientation of the polarizers 12 and retarders 24 as shown in FIG. 1, the four Stokes parameters can be determined from the electrical output signals 22 from the photodetectors 20 using the following set of equations:

$S_0 = I_T/I_T = 1$ $S_1 = (2I_1 - I_T)/I_T$ $S_2 = (2I_2 - I_T)/I_T$ $S_3 = (2I_3 - I_T)/I_T$

In the above set of equations, which can be calculated for each set of three polarizers 12 with different orientations and an open cell 24, $I_T$ is the total intensity of the infrared light 100 which passes through the open cell 24, $I_1$ is the intensity of the infrared light 100 which passes through the polarizer 12 oriented at 90° (also termed a vertical polarizer), $I_2$ is the intensity of the infrared light 100 which passes through the polarizer 12 oriented at 45°, and $I_3$ is the intensity of the infrared light 100 which passes through the polarizer 12 oriented at 0° and which includes a retarder 24 located thereabove. The retarder 24, which is also referred to as a quarter-wave plate, provides a $\pi/2$ phase shift of the infrared light 100 prior to the 0° polarizer.

In the example of FIG. 1, the polarizers 12 can comprise wire grid polarizers 12 which are formed from a plurality of parallel metal lines (also termed wire grids or grid lines) which are formed with a particular orientation. A spacing between adjacent grid lines in each polarizer 12 is smaller than the wavelength of the infrared light 100. This subwavelength spacing is necessary in order to provide a high polarization extinction ratio (i.e. a high TM/TE transmitted light ratio). In each polarizer 12, there is a strong anisotropic absorption of the infrared light 100 which is polarized parallel to the grid lines (i.e. TE-polarized light) while the infrared light 100 which is polarized perpendicular to the grid lines (i.e. TM-polarized light) is transmitted through the polarizer 12. Thus, the orientation of each polarizer 12 will determine how each polarization state of the infrared light 100 for a particular pixel will be filtered by that polarizer 12.

The size of each polarizer is determined largely by the lateral dimensions of the optical fibers 14 and the photodetectors 20. When the photodetectors 20 are provided in a focal plane array 28 having a large pixel count (e.g. 512×512 pixels), the lateral dimensions of each photodetector 20 will generally be about 30 µm or less, with the exact pixel size depending upon the wavelength of the infrared light 100 being detected. Thus, for example, a focal plane array 28 designed for 8-12 µm infrared light detection can have a pixel size of 30 µm; whereas a focal plane array 28 designed for 3-5 µm infrared light detection can have a smaller pixel size of about 10 µm. The optical fibers 14 can have a core diameter in the range of 10-100 µm, with the core diameter generally being about the same as the lateral dimensions of the photodetectors 20.

Each polarizer 12 can be formed with gold grid lines which can be, for example, about 0.2 µm wide with a pitch of 0.4 µm to provide a 50% duty cycle. A thin layer of titanium about 10 nanometers (nm) thick can be used beneath the gold grid lines to improve the adhesion of the gold grid lines which can be, for example, 0.15 µm high. The titanium layer improves the adhesion to the optical fibers 14 whereon the polarizers 12 are formed in the example of FIG. 1. The polarizers 12 can be formed using electron beam patterning of a resist (e.g. polymethyl methacrylate also termed PMMA) which is spun onto the optical fibers 14 which can be provided in a fiber optic faceplate 30. After developing the resist to provide a plurality of openings where the grid lines are to be formed, the titanium and gold can be deposited over the resist and in the openings. Liftoff of the resist and the titanium and gold deposited thereon can then be performed to leave the grid lines which form each polarizer 12.

Although the polarizers 12 and the open cell 26 are shown in FIG. 1 as being square, these elements can also be circular (see FIG. 4), rectangular, elliptical or any arbitrary shape. Each polarizer 12 and open cell 26 can be centered about one of the optical fibers 14 over a core 40 thereof wherein the infrared light 100 will be guided, and can optionally extend out over a cladding 42 of that optical fiber 14 (see FIG. 2).

The metal layers used to form the polarizers 12 can extend between the polarizers 12 to block any of the incident infrared light 100 which does not pass through the polarizers 12 or the open cells 26. Additionally, an infrared-absorbing material 32 can be provided around and between the optical fibers 14 in the fiber optic faceplate 30. This is useful to absorb any of the infrared light 100 which leaks out of the optical fibers 14 and which could otherwise result in crosstalk between the photodetectors 20. The infrared-absorbing material 32 can comprise, for example, epoxy.

The optical fibers 14 can comprise infrared optical fibers which transmit infrared light 100 over a particular wavelength band which can be in the wavelength range of 1.5 to 30 µm, with the exact wavelength band depending upon the type of photodetectors 20 used for the sensor 10. The infrared optical fibers 14 used in the sensor 10 can comprise different types of glass such as heavy metal fluoride glass (e.g. a fluorozirconate glass such as $ZrF_4$—$BaF_2$—$LaF_3$-$AlF_3$—NaF glass also known as ZBLAN; or a fluoroaluminate glass such as $AlF_3$—$ZrF_4$—$BaF_2$—$CaF_2$—$YF_3$), germanate glass, and chalcogenide glass (e.g. $As_2S_3$ or AsGeSeTe). The infrared optical fibers 14 can also comprise crystalline materials including polycrystalline AgBrCl and single-crystal sapphire. Heavy metal fluoride glass and single-crystal sapphire are useful for optical fibers 14 which transmit infrared light 100 at infrared wavelengths below about 5 µm. Polycrystalline AgBrCl, chalcogenide glass and germanate glass optical fibers 14 are useful at infrared wavelengths from about 3 µm up to about 20 µm.

The infrared optical fibers 14 can be arranged in a rectangular array with a spacing substantially equal to the spacing of the adjacent photodetectors 20 in the focal plane array 28. The fiber optic faceplate 30 formed from the infrared optical fibers 14 can be, for example, 0.5-2 millimeters thick with an entrance side and an exit side thereof both being polished. The optical fibers 14 extend between the entrance and exit sides of the fiber optic faceplate 30, which correspond to the entrance and exit ends 16 and 18 of the optical fibers 14. The optical fibers 14 can have a uniform outer diameter, or alternately can be tapered. A minifying taper for the optical fibers 14 can be useful, for example, to provide larger lateral dimensions for the entrance end 16 of the optical fibers 14 which, in turn, allows the use of a larger size for the polarizers 12 to reduce diffraction effects of the infrared light 100 which passes through the polarizers 12. The smaller lateral dimensions of the exit ends 18 optical fibers 14 with a minifying taper is useful to match the size of the photodetectors 20 and to prevent any cross-talk between adjacent photodetectors 20. An anti-reflection coating 34 can also be provided on the exit side of the fiber optic faceplate 30 to reduce a Fresnel reflection loss of the infrared light 100 being transmitted through the optical fibers 14.

The retarders 24 can be provided as a 2-D array formed on a substrate 36 which can be located above the fiber optic faceplate 30 with the retarders 24 facing the polarizers 12 with which the retarders 24 are used in order to minimize the distance therebetween. The substrate 36 is generally made of a material having a relatively high index of refraction and can comprise, for example, silicon or gallium arsenide (GaAs).

In the example of FIG. 1, one of the retarders 24 is located above each polarizer 12 which is aligned at 0° (i.e. each horizontal polarizer) without any retarders 24 being above the remaining polarizers 12 or the open cells 26. Each retarder 24 is a quarter-wave plate. The retarders 24 can be formed as subwavelength surface-relief gratings which utilize form birefringence to produce an effective refractive index difference, and thus a phase delay, between the TE and TM polarization components of the infrared light 100 which is transmitted through each retarder 24. The phase delay produced by each retarder 24 changes the polarization of the infrared light 100 transmitted through that retarder 24. This allows the retarders 24 to transform any of the infrared light 100 which is circularly-polarized into linearly polarized light 100, and vice versa.

The subwavelength surface-relief grating used to form each retarder 24 can comprise a series of substantially-equal linear ridges with formed in the substrate 36 by anisotropic etching. A fast axis of the subwavelength surface-relief grating is aligned along the direction of the ridges; and a slow axis is oriented at 90° to the direction of the ridges. The use of subwavelength surface-relief gratings to form a 2-D array of retarders 24 allows all of the retarders 24 to be formed simultaneously in a batch process, with the retarders 24 being substantially achromatic over a predetermined infrared wavelength range (e.g. 3-5 µm or 8-12 µm) for operation of the sensor 10.

The optical phase shift provided by a subwavelength surface-relief grating is determined by the substrate material in which the grating is formed and a depth of the material removed from the substrate to form the ridges. As an example, to form a one-quarter wavelength (i.e. $\pi/2$) retarder 24 for use over an infrared wavelength range 2-5 µm using a GaAs substrate 36, the depth of the material removed between adjacent ridges of the grating will be about 1.23 µm. A period of the subwavelength surface-relief grating can be, for example, 0.65 µm for use in this infrared wavelength range, with adjacent grating ridges being spaced apart by about 0.13 µm.

The subwavelength surface-relief grating for each retarder 24 can be fabricated in a batch process by first blanket depositing a thin layer (e.g. 30 nm thick) of silicon dioxide over the substrate 36 followed by a layer of an electron beam resist. Electron beam patterning of the resist layer can be used to define the lateral dimensions for each ridge of the grating. The resist layer can then be developed to provide openings where each ridge will be formed. Metal layers of titanium (about 20 nm thick) and nickel (about 120 nm thick) can then be blanket deposited over the substrate 36 and in the openings through the electron beam resist. The electron beam resist and the overlying metal layers can then be removed by lift-off to leave the titanium and nickel layers covering the areas where the ridges will be formed. Exposed regions of the silicon dioxide where the titanium and nickel layers are not present can then be etched using reactive ion etching to form an etch mask, with the substrate 36 between the ridges being exposed. The substrate 36 can then be etched down to the required depth between the ridges using a chemically-assisted ion beam etching step to form the ridges with substantially vertical sidewalls. When the substrate 36 comprises GaAs, the chemically assisted ion beam etching can be performed using an etch chemistry which comprises $Cl_2$, $BCl_3$ and Ar. The silicon dioxide and metal layers can then be removed by a wet etching step to complete the subwavelength surface-relief grating for each retarder 24. An anti-reflection coating can be applied to the substrate 36 on a side thereof opposite the retarders 24 to reduce a Fresnel reflection loss of the infrared light 100.

The focal plane array 28 can be a commercially-available focal plane array 28 having photodetectors 20 which sense the infrared light 100 over a predetermined wavelength range which can be, for example, anywhere within the range of 1.5-30 μm. Of particular interest are the atmospheric windows in the wavelength ranges of 3-5 μm and 8-12 μm.

The photodetectors 20 in the focal plane array 28 can comprise, for example, mercury-cadmium-telluride (MCT) photodetectors, indium antimonide photodetectors, or quantum-well photodetectors. The photodetectors 20 can be cooled to a relatively low temperature (e.g. generally from 200° K down to about 77° K) to provide an enhanced sensitivity for detection of the infrared light 100, and to provide a reduced noise level in the electrical output signals 22.

Figure 2:
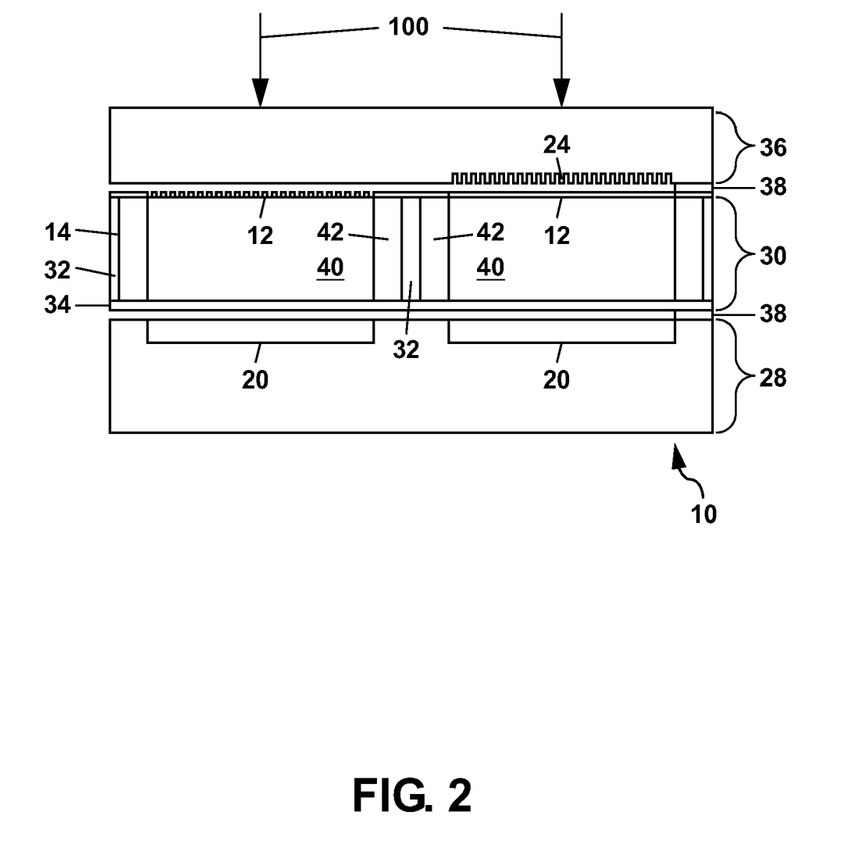
FIG. 2 shows a schematic cross-section view of a portion of the sensor of FIG. 1 along the section line 1-1 in FIG. 1.

The polarization-sensitive infrared imaging sensor 10 can be assembled by attaching the substrate 36 containing the 2-D array of retarders 24 to the fiber optic faceplate 30, and attaching the fiber optic faceplate 30 to the focal plane array 28. This can be done using an adhesive 38 (e.g. epoxy) to attach the elements 28, 30 and 36 together. The adhesive 38 can be on the order of a few microns thick to minimize diffraction effects of the infrared light 100. FIG. 2 shows a schematic cross-section view of a portion of the sensor 10 along the section line 1-1 in FIG. 1 after the various elements 28, 30 and 36 have been attached together.

The polarizers 12 must be located at the entrance end 16 of the optical fibers 14 rather than on the exit end 18 thereof since the optical fibers 14 can scramble the polarization of the infrared light 100 transmitted through the optical fibers 14. Any scrambling of the polarization of the infrared light 100 prior to filtering of the light 100 by the polarizers 12 would be deleterious to the operation of the sensor 10 if the polarizers 12 were to be located on the exit side 18 of the optical fibers 14 and facing the photodetectors 20. However, with the arrangement of the polarizers 12 on the entrance end 16 of the optical fibers 14, the polarization filtering is completed prior to transmission of the infrared light 100 through the optical fibers 14 so that any polarization scrambling by the optical fibers 14 does not affect performance of the sensor 10 since the photodetectors 20 only detect the intensity of the transmitted infrared light 100 and are not sensitive to any change in polarization of the infrared light 100 produced by the optical fibers 14. Thus, the arrangement of the polarizers 12 away from the photodetectors 20 in the present invention is contrary to conventional snapshot polarimeters which locate the polarizers as close to the photodetectors as possible.

Figure 3:
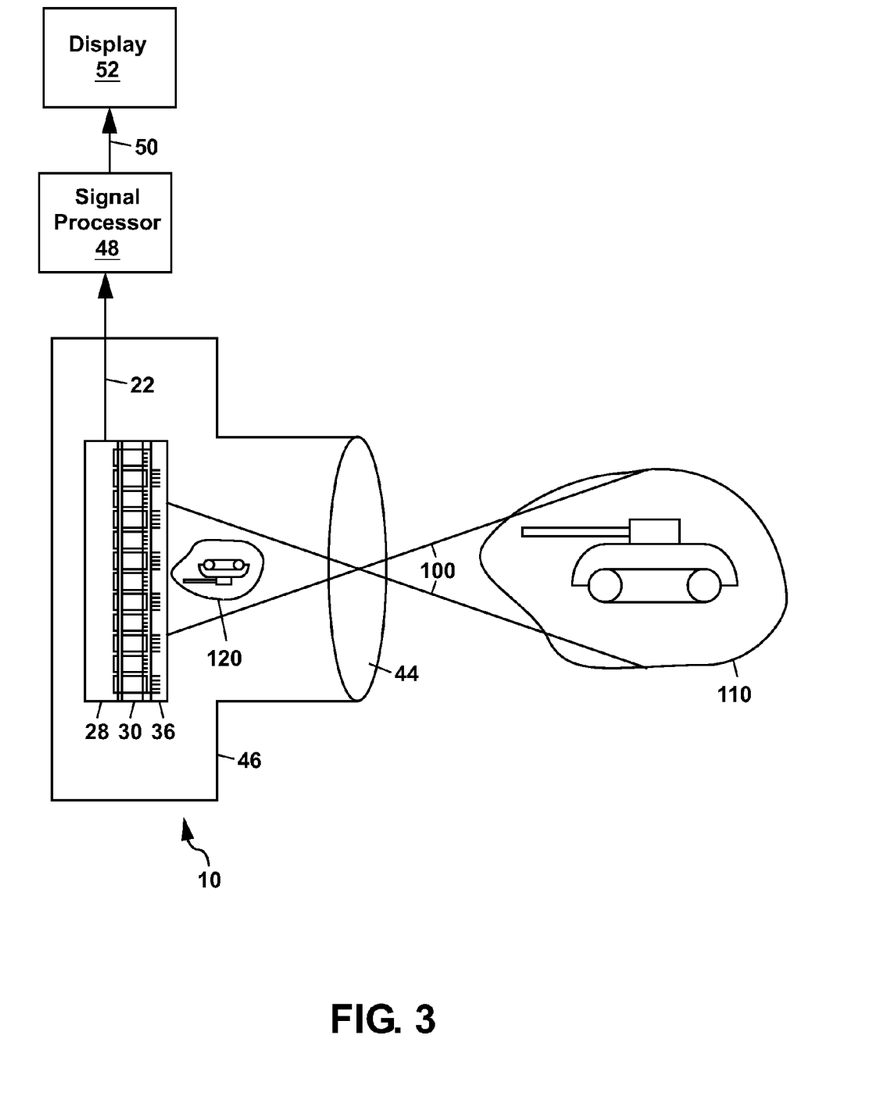
FIG. 3 shows a schematic cross-section view of the polarization-sensitive infrared image sensor of FIG. 1 with imaging optics and a signal processor and display.

FIG. 3 shows a schematic cross-section view of the sensor 10 of FIG. 1 including imaging optics 44 to image the infrared light 100 from a scene 110 onto the sensor 10. The sensor 10 can be located in a housing 46 which can include cooling means in the form of a thermoelectric or thermionic cooler, or a cryostat to cool the sensor 10 to a low temperature between 200° K and 77° K. The imaging optics 44 can comprise one or more lenses or mirrors to form an infrared light image 120 of the scene 110 at a focal plane of the sensor 10 (e.g. at the 2-D array of polarizers 12).

The 2-D array of polarizers 12 and the open cells 26 in the sensor 10 spatially filter the infrared light 100 by dividing the infrared light image 120 into a plurality of pixels. Additional polarization filtering of the pixels is provided by the polarizers 12. The polarization-filtered infrared light 100 passing through each polarizer 12 and the infrared light 100 passing through the open cells 26 are then directed through the optical fibers 14 to the infrared photodetectors 20 located therebeneath. Each infrared photodetector 20 detects one of the pixels of the infrared image 120 and generates an electrical output signal 22 containing polarization information for that pixel. Electronic circuitry can be provided in the focal plane array 28 to allow the electrical output signals 22 from the photodetectors 20 to be amplified and to be output either serially or in parallel to a signal processor 48.

The signal processor 48 can comprise a computer or microprocessor and can be used in various ways to process the electrical output signals 22 and to generate an output signal 50 which can be provided to a display 52. The signal processor 48 can be used, for example, to generate an image for a particular polarization state (e.g. vertically polarized, horizontally polarized, left-circular polarized, or right-circular polarized) of the infrared light 100 by using the electrical output signals 22 from the photodetectors 20 which detect that particular polarization state of the infrared light 100. The signal processor 48 can also be used to compute one or more of the Stokes parameters $S_0$, $S_1$, $S_2$ and $S_3$ and to provide an image of the scene 110 on the display 52 for a particular Stokes parameter $S_0$, $S_1$, $S_2$ or $S_3$.

The signal processor 48 can also be used to compute the full Stokes vector $\overline{S}$ which can then be used to form a super pixel of a polarization-sensitive image of the scene 110. The term "super pixel" as used herein refers to a portion of a polarization-sensitive image of the scene 110 which is formed using at least three Stokes parameters, and preferably all four Stokes parameters.

Figure 4:
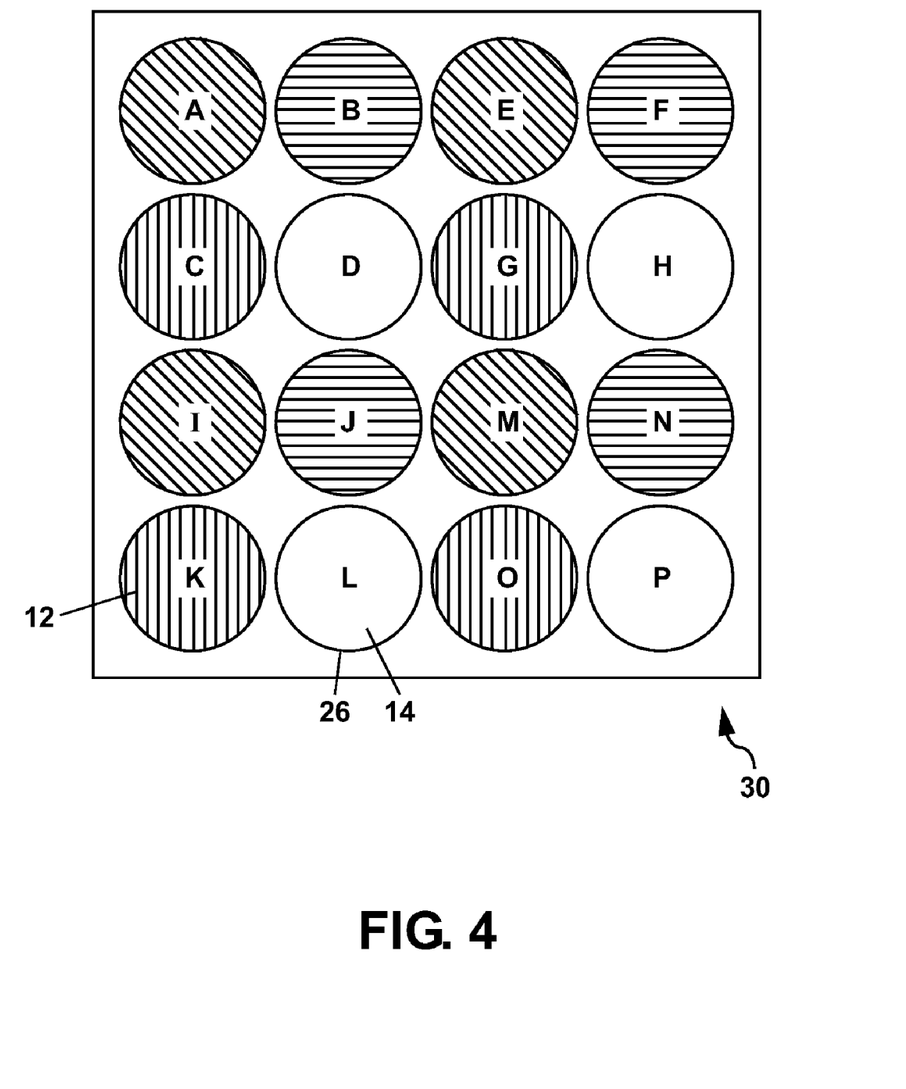
FIG. 4 shows a schematic plan view of a portion of the fiber optic faceplate with the polarizers and open cells located thereon to illustrate ways in which a super pixel can be formed.

FIG. 4 is presented herein to illustrate the formation of super pixels for a polarization-sensitive image. FIG. 4 shows a schematic plan view of a portion of a fiber optic faceplate 30 containing a plurality of polarizers 12 and open cells 26 formed on the optical fibers 14 in the faceplate 30. The polarizers 12 and open cells 26 divide an incident infrared light image 120 into a plurality of pixels labelled A, B, C, . . . , P. Each pixel is detected by a separate photodetector 20 to provide an electrical output signal 22 corresponding to that pixel. The electrical output signals 22 for each set of four adjacent pixels in FIG. 4 can be combined in the signal processor 48 to compute the Stokes vector $\overline{S}$ which is then used to generate a different super pixel. Thus, the pixels A, B, C and D can be used to generate a first super pixel; the pixels E, F, G and H can be used to generate a second super pixel; the pixels I, J, K and L can be used to generate a third super pixel; and the pixels M, N, O and P can be used to generate a fourth super pixel. This can continue for all of the pixels in the infrared light image 120. With this combination of pixels, an infrared light image 120 having a 512×512 array of pixels can be used to generate a polarization-sensitive image of the scene 110 having 256×256 super pixels.

A higher-resolution super pixel image can be obtained if the polarization information from each pixel is used in forming multiple super pixels. This can be done, for example, by using the pixels A, B, C and D to generate one super pixel; using the pixels B, E, D and G to generate another super pixel;

using the pixels E, F, G and H to generate yet another super pixel; and so on. Using this combination of pixels to form each super pixel, the resolution of the polarization-sensitive image of the scene 110 can be increased to (M−1)×(N−1) for an M×N array of photodetectors 20.

Figure 5:
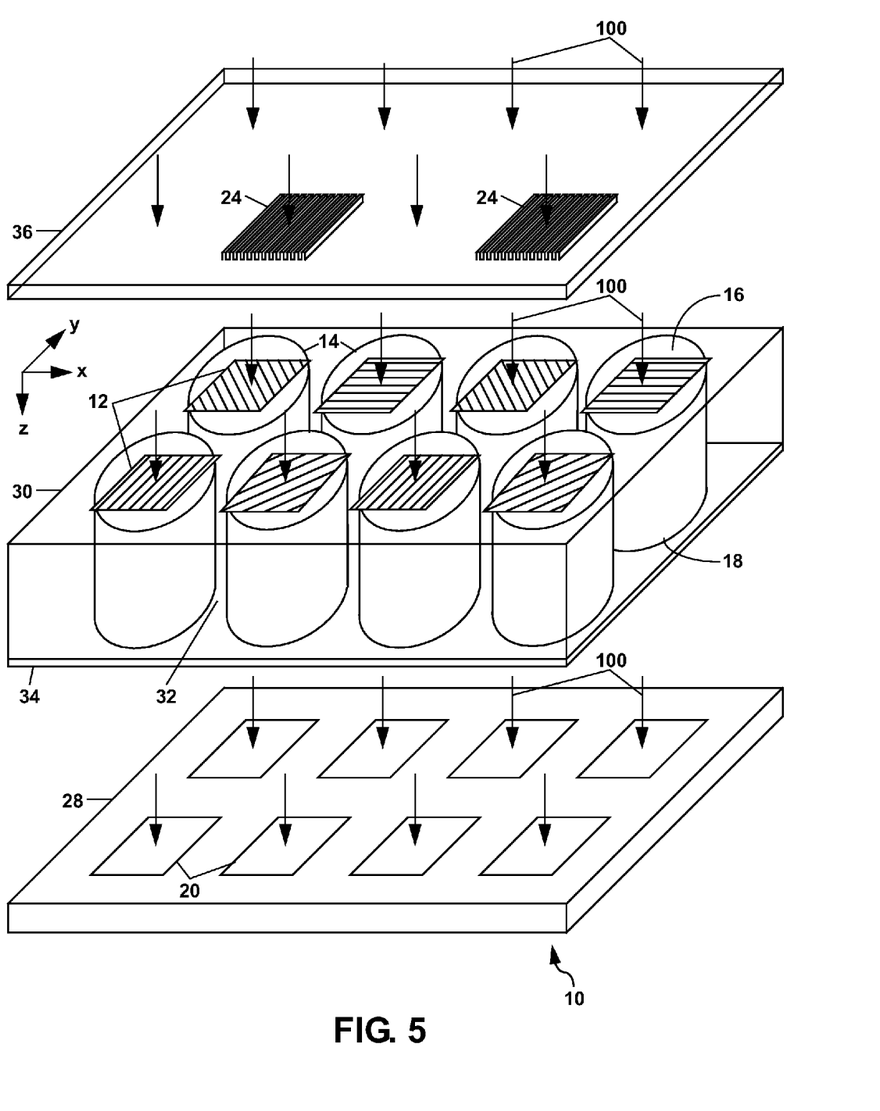
FIG. 5 shows a second example of the polarization-sensitive infrared image sensor of the present invention.

Other arrangements for the polarizers 12 in the polarization-sensitive infrared image sensor 10 of the present invention are possible. FIG. 5 shows an exploded perspective view of a second example of the polarization-sensitive infrared image sensor 10 of the present invention. In this example of the sensor 10, a polarizer 12 aligned diagonally at an angle of 135° (also referred to as −45°) with respect to the horizontal x-axis is used in place of each open cell 26 in FIG. 1, with the retarders 24 being located above the 135° polarizers.

In this second example, the four Stokes parameters can be determined from the electrical output signals 22 from the various photodetectors 20 using the following set of equations:

$$S_0 = I_T/I_T = 1$$

$$S_1 = (2I_1 - I_T)/I_T$$

$$S_2 = (2I_2 - I_T)/I_T$$

$$S_3 = (2I_3 - I_T)/I_T$$

In the above set of equations, which can be calculated for each set of four adjacent polarizers 12 with different orientations, $I_T$ is the combined intensity of the infrared light 100 which passes through the polarizers 12 oriented at 0° and 90° (i.e. the horizontal polarizer and the vertical polarizer, respectively) multiplied by a scaling factor $\Gamma$ which compensates for an attenuation of the 0° and 90° polarizers at different distances and input polarizations of the infrared light 100, $I_1$ is the intensity of the infrared light 100 which passes through the polarizer 12 oriented at 90° (or alternately the intensity of the polarizer 12 oriented at 0°), $I_2$ is the intensity of the infrared light 100 which passes through the polarizer 12 oriented at 45°, and $I_3$ is the intensity of the infrared light 100 which passes through the polarizer 12 which is aligned at 135° and which includes a retarder 24 located thereabove to provide a $\pi/2$ phase shift of the infrared light 100 prior to filtering of the light 100 by the 135° polarizer.

Those skilled in the art will understand that other arrangements of the polarizers 12 and the open cells 26 are possible. As an example, the 45° and 135° polarizers 12 can be located along either the x-axis or the y-axis rather than diagonally as shown in FIG. 5. As another example, the open cells 26 of FIG. 1 can be used with polarizers 12 which are oriented at 0°, 45° and 135°.

In yet other embodiments of the present invention, the retarders 24 can be formed on the fiber optic faceplate 30 or etched into the optical fibers 14; and the polarizers 12 can be provided on the substrate 36. In these embodiments, the substrate 36 can comprise glass, fused silica, or quartz. In these embodiments of the present invention, the polarizers 12 preferably face the fiber optic faceplate 30 to minimize the distance therebetween and thereby minimize diffraction of the infrared light 100 which could otherwise result in crosstalk between adjacent pixels in the polarization-sensitive infrared image sensor 10.

The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A polarization-sensitive infrared image sensor, comprising:
   a two-dimensional (2-D) array of polarizers to receive infrared light from a scene and to filter the infrared light according to polarization;
   a 2-D array of optical fibers located proximate to the 2-D array of polarizers to receive the filtered infrared light from each polarizer at an entrance end of the 2-D array of optical fibers and to transmit the filtered infrared light to an exit end thereof; and
   a 2-D array of infrared photodetectors located proximate to the exit end of the 2-D array of optical fibers, each infrared photodetector detecting the filtered infrared light from one of the optical fibers to generate an electrical output signal containing polarization information for a pixel of the scene.

2. The apparatus of claim 1 further comprising a signal processor to receive the electrical output signal from a plurality of adjacent infrared photodetectors in the 2-D array of photodetectors and to form therefrom a super pixel of a polarization-sensitive image of the scene.

3. The apparatus of claim 2 further comprising a display connected to the signal processor to display the polarization-sensitive image of the scene.

4. The apparatus of claim 1 further comprising imaging optics to image the infrared light from the scene onto the 2-D array of polarizers.

5. The apparatus of claim 1 further comprising a 2-D array of retarders located in front of the 2-D array of polarizers to provide an optical phase shift of the infrared light prior to filtering the infrared light by the polarizers.

6. The apparatus of claim 5 wherein each retarder is a quarter-wave plate.

7. The apparatus of claim 5 wherein each retarder comprises a subwavelength surface-relief grating.

8. The apparatus of claim 1 wherein each polarizer comprises a wire grid polarizer.

9. The apparatus of claim 1 wherein each polarizer is formed on the entrance end of one of the optical fibers.

10. The apparatus of claim 1 wherein each the 2-D array of optical fibers is formed as a fiber optic faceplate.

11. The apparatus of claim 10 wherein the fiber optic faceplate includes an infrared-absorbing material disposed between the optical fibers.

12. The apparatus of claim 10 wherein the fiber optic faceplate includes an anti-reflection coating on a surface thereof.

13. A polarization-sensitive infrared image sensor, comprising:
   a two-dimensional (2-D) array of wire grid polarizers to receive infrared light image of a scene and to divide the infrared light image into a plurality of pixels with each pixel being filtered according to polarization by one of the wire grid polarizers;
   an infrared fiber optic faceplate comprising a 2-D array of optical fibers, with the infrared fiber optic faceplate being located proximate to the 2-D array of wire grid polarizers and with each optical fiber receiving the filtered one of the pixels and directing that pixel to an exit end of that optical fiber; and
   an infrared photodetector located proximate to the exit end of each optical fiber to sense the pixel and to generate therefrom an electrical output signal containing the polarization information of that pixel.

14. The apparatus of claim 13 further comprising a signal processor to combine the electrical output signals from a plurality of adjacent infrared photodetectors to form a super pixel of a polarization-sensitive image of the scene, and a display to display the polarization-sensitive image of the scene.

15. The apparatus of claim 13 wherein the 2-D array of wire grid polarizers are formed on an entrance side of the infrared fiber optic faceplate with each wire grid polarizer being centered on one of the optical fibers.

16. The apparatus of claim 13 further comprising a retarder located proximate to at least one of the wire grid polarizers to provide an optical phase shift of the pixel being filtered by that wire grid polarizer.

17. The apparatus of claim 16 wherein the retarder comprises a subwavelength surface-relief grating.

18. The apparatus of claim 16 wherein the optical fibers in the infrared fiber optic faceplate are separated by an infrared-absorbing material.

19. A polarization-sensitive infrared image sensor, comprising:
- a substrate having a plurality of retarders formed thereon, with the plurality of retarders being spaced apart, and with each retarder providing an optical phase shift for infrared light from a scene which is incident on that retarder;
- an infrared fiber optic faceplate located proximate to the plurality of retarders, with the infrared fiber optic faceplate having an entrance side and an exit side and comprising a plurality of optical fibers extending therebetween;
- a plurality of wire grid polarizers formed on the entrance side of the infrared fiber optic faceplate, with each wire grid polarizer being centered on one of the optical fibers to filter the infrared light according to polarization, with the polarization-filtered infrared light then being transmitted through that optical fiber to the exit side;
- a focal plane array detector located proximate to the exit side of the infrared fiber optic faceplate and comprising a two-dimensional (2-D) array of infrared photodetectors, with each infrared photodetector being located proximate to one of the optical fibers to detect the polarization-filtered infrared light transmitted through that optical fiber and generate an electrical output signal therefrom; and
- a signal processor to combine the electrical output signals from a plurality of the infrared photodetectors which are adjacent to each other to generate a polarization-sensitive image of the scene.

20. The apparatus of claim 19 further comprising infrared imaging optics to image the infrared light from the scene onto the plurality of retarders.

21. The apparatus of claim 19 wherein each retarder comprises a subwavelength surface-relief grating.

22. The apparatus of claim 19 wherein the infrared fiber optic faceplate includes an infrared-absorbing material disposed between the optical fibers therein.

23. The apparatus of claim 19 wherein the fiber optic faceplate has an anti-reflection coating on the exit side thereof.

24. The apparatus of claim 19 wherein the focal plane array detector is attached to the infrared fiber optic faceplate on the exit side thereof.

25. The apparatus of claim 24 wherein the substrate containing the plurality of retarders is attached to the infrared fiber optic faceplate on the entrance side thereof.

* * * * *